US00PP15061P2

(12) United States Plant Patent
Zary

(10) Patent No.: US PP15,061 P2
(45) Date of Patent: Aug. 3, 2004

(54) SHRUB ROSE PLANT NAMED 'JACTANRE'

(50) Latin Name: *Rosa hybrida*
Varietal Denomination: JACtanre

(75) Inventor: Keith W. Zary, Somis, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/697,516

(22) Filed: Oct. 29, 2003

(51) Int. Cl.[7] ..... A01H 5/00
(52) U.S. Cl. ..... Plt./108
(58) Field of Search ..... Plt./108

*Primary Examiner*—Anne Marie Grunberg
*Assistant Examiner*—S. B. McCormick-Ewoldt
(74) *Attorney, Agent, or Firm*—Klarquist Sparkman LLP

(57) ABSTRACT

Hybrid tea rose plant having large red with lighter reverse flower; vigorous upright growth; ability to grow vigorously on its own roots; excellent hybrid tea flower form; dark, glossy green foliage; and resistance to rust and powdery mildew.

1 Drawing Sheet

Genus and species: Rosa hybrida.
Variety denomination: 'JACtanre'.

ORIGIN OF THE INVENTION

The present invention relates to a new and distinct variety of a shrub rose plant named 'JACtanre' which was originated by me by crossing two unnamed, unpatented varieties.

BACKGROUND OF THE INVENTION

The primary objective of this breeding was to produce a new rose variety having the more compact plant and bright glossy foliage of the female parent combined with the deep red of the male parent's flower.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Large red with lighter reverse flower;
2. Vigorous, upright growth;
3. Ability to grow vigorously on its own roots;
4. Excellent hybrid tea flower form;
5. Dark, glossy green foliage.
6. Resistance to rust and powdery mildew.

Asexual reproduction of this new variety by cuttings, as performed at Somis, Calif., shows that the foregoing and all other characteristics and distinctions come true to form and are established and transmitted through succeeding propagations.

Comparison with Parents

The subject variety differs in that the male parent is exceptionally tall and has pure red flowers. JACtanre is more compact in height and has red flowers with a light reverse. The female parent has pink flowers and is very compact.

Comparison with Similar Variety

The closest commercial variety is 'JACtwin' (U.S. Plant Pat. No. 4,437). It differs from 'JACtwin' in flower size in that the flowers of 'JACtanre' are much larger, and in flower presentation, 'JACtwin' is a grandiflora and presents flowers in clusters.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:

*Seed parent.*—Unnamed seedling. Not patented. (Unnamed)×(Unnamed).

*Pollen parent.*—Unnamed seedling. Not patented. (Unnamed)×(Ingrid Bergman).

FLOWER

Observations made from plants commencing at eighteen months of age grown in a garden environment at Somis, Calif.

Blooming habit: Continuous.

Bud:

*Size.*—About 5.5 cm long and 4 cm in diameter when the petals start to unfurl.

*Form.*—The bud form is long, pointed ovoid.

*Color.*—When sepals first divide, bud color is Red Group 46A. When half blown, the upper sides of the petals are Red Group 53B with Yellow Group 12B at base; and the lower sides of the petals are White Group 155B on bottom one-third; Red Group 56C on top two-thirds and Yellow Group 12C at base.

*Sepals.*—Color: Upper surface: Prominently Yellow-Green Group 144D, turning to Yellow-Green Group 144B toward the outer margins; frequently overlayed with Greyed-Red Group 181B. Lower surface: Green Group 143C with occasional overlaying of Greyed-Red Group 180A. Length: 30–40 mm. Width: 12–15 mm. Shape: Subulate. Surface texture: Upper surface: Canescent. Lower surface: Pubescent. Margin: Cililate. There are three normally appendaged sepals. There are two unappendaged sepals with hairy edges.

*Receptacle.*—Color: Green Group 143C. Shape: Funnel. Size: Small, slender, about 1 cm long×0.5 cm wide. Surface: Smooth, glabrous.

*Peduncle.*—Length: Medium, averaging about 6 cm. Surface: Prickly, glandular, occasional small prickles. Color: Greyed-Purple Group 183A. Strength: Stiff, erect.

Bloom:

*Size.*—Large. Average open diameter is about 10–12 cm.

*Borne.*—Singly.

*Stems.*—Strength: Strong. Average length is about 30–40 cm with a diameter of 5–7 mm.

*Form.*—When first open: High centered. Permanence: Quill fashion.

*Petalage.*—Number of petals under normal conditions: 35.

*Color.*—The upper sides of the petals are Red Group 53B. The reverse sides of the petals are White Group 155B on bottom one-third, Red Group 56C on top two-thirds. The base of each petal is Yellow Group 12B. The major color on the upper side is Red Group 53B. Occasional blackening on petal apex of outer petals under growing condition of 35° C. or higher.

*Variegations.*—None.

*Discoloration.*—The general tonality at the end of the first day: Red Group 53B. At the end of the third day: Red Group 53B with Red Group 56C on petal reverse. Further aging: Fades to Red Group 53D by day six, petals drop by day nine.

*Fragrance.*—Slight, damask.

Petals:

*Texture.*—Thick; coriaceous.

*Shape.*—Orbicular.

*Surface.*—Smooth.

*Margin.*—Entire. Apex Shape: Obtuse. Base Shape: Rounded.

*Form.*—Moderately quilled.

*Arrangement.*—Imbricated.

*Petaloids.*—Number: 3–5 Color: Red Group 46A with White Group 155B at base. Size: 2.5 cm long and 3.0 cm wide.

*Persistence.*—Petals drop off cleanly before drying.

*Lastingness.*—On the plant: Long (about nine days). As a cut flower: Long (about 9–10 days).

Reproductive parts:

*Stamens.*—Number: 80–90. Length: 18–22 mm. Arrangement: Anthers: Length: 3 mm. Color: Yellow-Orange Group 22C. Filaments: Color: Yellow Group 16C. Length: 15–19 mm. Pollen: Color: Orange Group 26C.

*Pistils.*—Number: 30–35. Length: 6–8 mm. Styles: Color: Red Group 45B. Length: 5–7 mm. Stigmas: Color: Yellow-White Group 158A. Length: 1 mm.

*Hips.*—None observed.

PLANT

*Form.*—Bush.

*Growth.*—Vigorous, medium, upright, branching.

*Age at maturity.*—2 years.

*Mature plant.*—Height: 150 cm. Width: 100 cm.

*Rootstock.*—Own roots.

Foliage: Number of leaflets on normal mid-stem leaves: 5.

*Size.*—About 13 cm long×10 cm wide.

*Quantity.*—Abundant.

*Color.*—New foliage: Upper side: Greyed Red Group 183A. Lower side: Greyed Red Group 183B. Old foliage: Upper side: Green Group 139A. Lower side: Green Group 139B.

Leaflets:

*Size.*—About 5 cm long×3.5 cm wide.

*Shape.*—Broadly oval.

*Base shape.*—Rounded.

*Apex shape.*—Acuminate.

*Texture.*—Leathery, glossy.

*Edge.*—Serrated.

*Serrations.*—Single.

*Petiole.*—Color: Green Group 139D.

*Petiole rachis.*—Color: Green Group 146D. Underside: Rough with prickles and occasional glands.

*Auricle shape, if present.*—None.

*Stipules.*—Length: 17–18 mm, serrated, bearded. Shape: Adnate.

*Disease resistance.*—Resistant to mildew and rust and susceptible to blackspot under normal growing conditions.

*Pest resistance.*—None noted.

*Vein color.*—Green Group 139A.

*Venation pattern.*—Reticulate.

Wood:

*New wood.*—Color: Greyed Purple Group 183A. Bark: Smooth.

*Old wood.*—Color: Yellow Green Group 146B. Bark: Smooth.

Prickles:

*Quantity.*—On main canes from base: Ordinary. On laterals from main canes: Ordinary.

*Form.*—Hooked downward.

*Length.*—6–10 mm.

*Color when young.*—Greyed Purple Group 183A.

*Color when mature.*—Greyed Orange Group 177A.

Small prickles:

*Quantity.*—On main stalks: Few. On laterals: Few.

*Color.*—Same as for large thorns.

Winter hardiness: Hardy to Zone 5.

I claim:

1. A new and distinct variety of rose plant of the hybrid tea class, substantially as herein shown and described, characterized particularly by its large red with lighter reverse flower; vigorous upright growth; ability to grow vigorously on its own roots; excellent hybrid tea flower form; dark, glossy green foliage, and resistance to rust and powdery mildew.

* * * * *

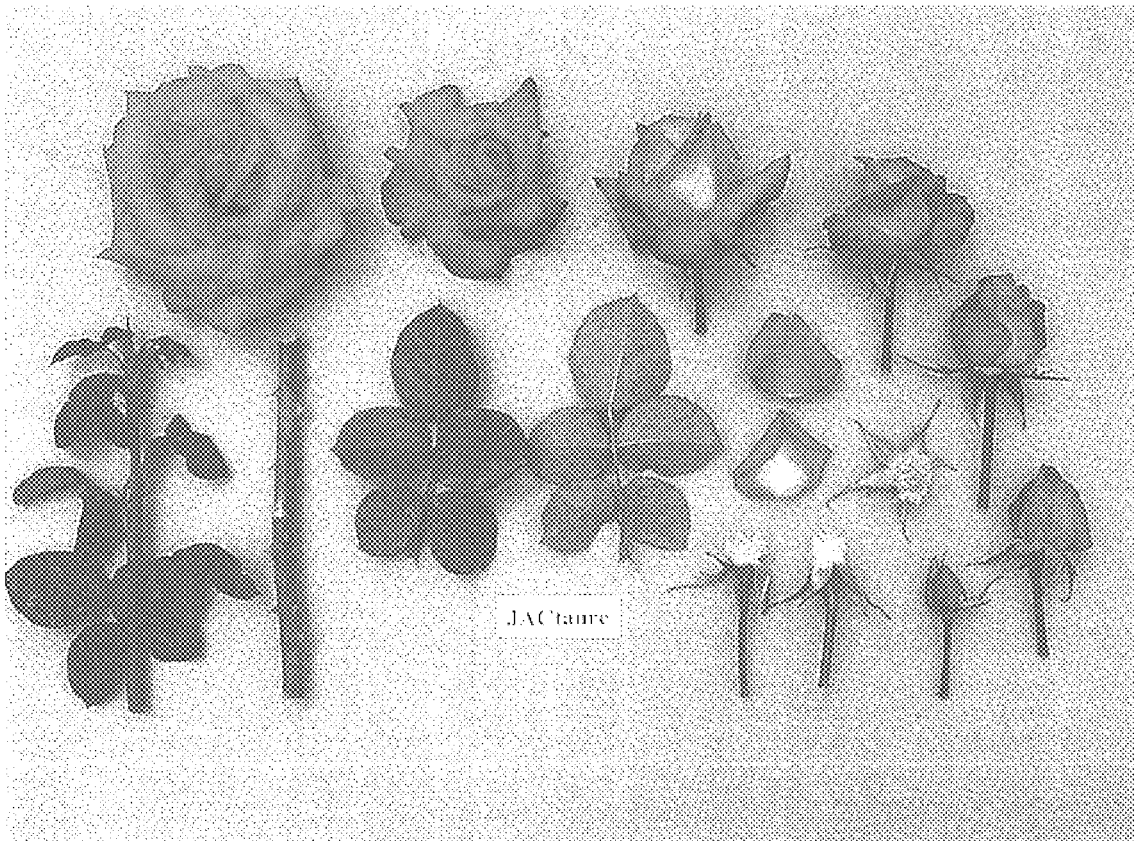
J.A.Chaire